United States Patent [19]

Kórósi et al.

[11] 4,322,346
[45] Mar. 30, 1982

[54] 5H-2,3-BENZODIAZEPINE DERIVATIVES

[76] Inventors: Jenó Kórósi, 27, Attila ut; Tibor Láng, 11, Fenyöu., both of Budapest I; József Székely, 43, Rudas L. u., Budapest VI; Ferenc Andrasi, 42, Szeruskert u., Budapest III; Gábor Zólyomi, 9a, Dolgozo u., Budapest SVIII; József Borsi, 90, Bartok Bela u.; Katalin Goldschmidt née Horváth, 28, Alsohegy u., both of Budapest XI; Tamás Hámori, 34, Egri u., Maklar; Gabriella Szabó née Czibula, 13d, Martos F. u., Budapest XIV; Zsuzsanna Meszaros née Dunai-Kovacs, 66, Izabella u., Budapest VI; Erzsébet Miglecz, 27, Attila u., Budapest I, all of Hungary

[21] Appl. No.: 191,811

[22] Filed: Sep. 26, 1980

Related U.S. Application Data

[63] Continuation-in-part of Ser. No. 86,047, Oct. 18, 1979, abandoned.

[30] Foreign Application Priority Data

Oct. 19, 1978 [HU] Hungary .................... GO 1426

[51] Int. Cl.³ .................. A61K 31/55; C07D 243/00; C07D 407/04; C07D 409/04
[52] U.S. Cl. ..................... 260/239 BD; 260/345.2; 260/347.7; 424/244; 424/275; 424/285; 560/52; 562/460; 568/332; 568/333
[58] Field of Search ............. 260/239 BD, 347.7

[56] References Cited

U.S. PATENT DOCUMENTS

Re. 30,014  5/1979  Korosi et al. ............. 260/239 BD
3,736,315  5/1973  Korosi et al. ............. 260/239 BD

OTHER PUBLICATIONS

Reid, et al., J. Chem. Soc., Perkin I, pp. 2543–2551, (1973).

Primary Examiner—Alton D. Rollins
Attorney, Agent, or Firm—Young & Thompson

[57] ABSTRACT

New 5H-2,3-benzodiazepine derivatives of the formula

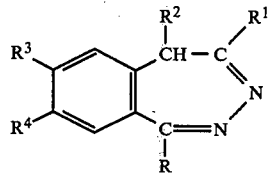

wherein
R is phenyl having a trifluoromethyl or halogen substituent,
$R^1$ is methyl,
$R^2$ is hydrogen,
$R^3$ is methoxy and $R^4$ is methoxy, and the pharmaceutically acceptable acid addition salts thereof, are potent tranquilizers.

3 Claims, No Drawings

5H-2,3-BENZODIAZEPINE DERIVATIVES

The present application is a continuation-in-part of our copending application Ser. No. 86,047, filed Oct. 18, 1979, abandoned.

The invention relates to new 5H-2,3-benzodiazepine derivatives and acid addition salts thereof.

The new compounds according to the invention correspond to the general formula (I),

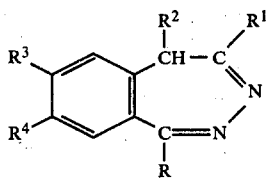

wherein

R stands for a phenyl group having optionally a $C_{1-3}$ alkyl, a trifluoromethyl or a nitro, or 1 to 3 halogen, hydroxy and/or $C_{1-3}$ alkoxy substituent(s), or a heterocyclic group containing 1 or 2 nitrogen, oxygen and/or sulfur atom(s), $R^1$ stands for a $C_{1-4}$ alkyl, hydroxymethyl, formyl, carboxy or carbalkoxy group, $R^2$ stands for a hydrogen atom or a $C_{1-4}$ alkyl, dialkylaminoalkyl, alkylamino or dialkylamino group, $R^3$ represents a hydrogen atom, a hydroxy, $C_{1-3}$ alkyl, $C_{1-5}$ alkoxy or di($C_{1-3}$ alkyl)amino-$C_{1-3}$ alkoxy group, and $R^4$ stands for a hydrogen atom, a hydroxyl, $C_{1-3}$ alkyl or $C_{1-3}$ alkoxy group or a halogen atom, with the proviso that if R represents 3,4-dimethoxyphenyl group, $R^1$ is methyl group and $R^2$ is ethyl group, $R^3$ and $R^4$ may not stand for methoxy group, or a pharmaceutically acceptable acid addition salt thereof.

The new compounds of the general formula (I) possess more significant central nervous effects than 1-(3,4-dimethoxyphenyl)-4-methyl-5-ethyl-7,8-dimethoxy-5H-2,3-benzodiazepine (tofizopam or Grandaxin), the only 5H-2,3-benzodiazepine compound synthetized till now. The synthesis and biological properties of Grandaxin are described in the Hungarian Pat. specification No. 155,572, U.S. Pat. No. 3,736,315 and Swiss Pat. No. 519,507.

The new compounds of the general formula (I) or their salts can be prepared by reacting a 1,5-diketone of the general formula (II),

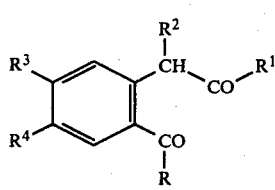

wherein R, $R^1$, $R^2$, $R^3$ and $R^4$ are as defined above, a 2-benzopyrilium salt of the general formula (III),

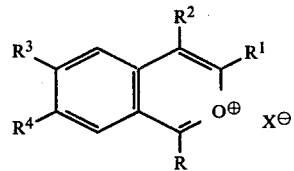

wherein R, $R^1$, $R^2$, $R^3$ and $R^4$ are as defined above and X stands for chloride, iodide, tetrafluoroborate, tetrachloroferrate, hexachlorostannate, hydrosulfate, dihydrophosphate or perchlorate anion, a 6H-2-benzopyran-6-one of the general formula (IV),

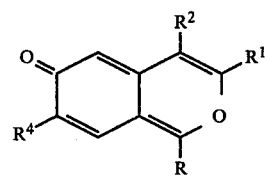

wherein R, $R^1$, $R^2$ and $R^4$ are as defined above, or an isochromene compound of the general formula (V),

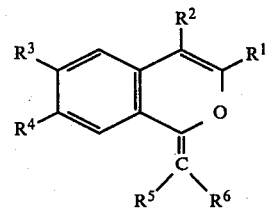

wherein R, $R^1$, $R^2$, $R^3$ and $R^4$ are as defined above and $R^5$ and $R^6$ each represent hydrogen atom, a $C_{1-3}$ alkyl group or a group corresponding to the above definition of substituent R, with 1 to 5 moles of hydrazine, hydrazine hydrate or a hydrazine $C_{1-3}$ carboxylate in a polar solvent, preferably in water, a $C_{1-4}$ alcohol, a $C_{1-3}$ carboxylic acid, dioxane, dimethyl formamide, pyridine or mixtures thereof, at a temperature of $-20°$ C. to $120°$ C., preferably at $60°$ C. to $100°$ C. When a compound of the general formula (II), wherein R is an aryl group or a heterocyclic group, is applied as starting substance, a mineral acid, such as hydrochloric acid or sulfuric acid, is added to the reaction mixture after reacting the starting substance with hydrazine in order to facilitate cyclocondensation. If desired, the resulting compounds of the general formula (I) can be converted into other derivatives having the general formula (I), and/or, if desired, the free bases of the general formula (I) can be converted into their pharmaceutically acceptable acid addition salts, or the salts of the 5H-2,3-benzodiazepine derivatives of the general formula (I) can be converted into the free bases or into other acid addition salts.

The compounds of the general formula (I) can be converted into other derivatives falling within the scope of the same general formula e.g. by the following reactions:

(a) the compounds of the general formula (I), wherein any of R, $R^1$, $R^3$ and $R^4$ represents hydroxy group or a hydroxy-bearing substituent, can be alkylated, aralkylated or acylated in a manner known per se;

(b) the 5H-2,3-benzodiazepine-4-carboxylates can be reduced with a metal hydride, such as sodium borohydride, to form the respective 4-hydroxymethyl-5H-2,3-benzodiazepine compounds;

(c) The 5H-2,3-benzodiazepine-4-carboxylates can be saponified into the appropriate 4-carboxylic acids, and these latter compounds can be decarboxylated to form the respective 4-unsubstituted 5H-2,3-benzodiazepine derivatives;

(d) the 4-methyl-5H-2,3-benzodiazepine derivatives can be oxidized with selenium dioxide into the respective 4-formyl compounds.

The pharmaceutically acceptable acid addition salts of the compounds having the general formula (I) can be prepared by reacting the free bases e.g. with hydrochloric, hydrobromic, phosphoric, sulfuric or perchloric acid. When any of the substituents attached to the benzodiazepine ring contains a more basic nitrogen atom, organic acids, such as acetic, tartaric, lactic, maleic or fumeric acid, can also be applied as salt-forming agents.

The 5H-2,3-benzodiazepine derivatives of the general formula (I) are generally purified before the salt formation step, however, the crude bases, however, can also be subjected to salt formation. If a free base of the general formula (I) is difficult to crystallize, it is preferred to convert it into a well crystallizable salt, such as rhodanate or hydrochloride, from which the base can be liberated in pure state, if desired.

If a 2-benzopyrilium salt of the general formula (III) is applied as starting substance, the reaction is performed in the presence of an acid binding agent. Conveniently an excess of hydrazine or hydrazine hydrate is used as acid binding agent, but alkali metal hydroxides, carbonates, hydrocarbonates or organic bases, e.g. pyridine or triethylamine, can be applied as well. If necessary, the starting substances of the general formulae (II), (III), (IV) and (V) can be converted into each other prior to reacting them with the hydrazine reactant. According to a preferred method the hydrazine reactant is added directly into the resulting reaction mixture.

The compounds of the general formulae (II), (III) and (IV), utilized as starting substances in the preparation of the benzodiazepine derivatives of the general formula (I), are described in or can be prepared according to the following references: Ber. Deut. Chem. Ges. 75, 891 (1942), 76, 855 (1943), 77, 6, 343 (1944); J. Am. Chem. Soc. 72, 1118 (1950); Acta Chim. Acad. Sci. Hung. 40, 295 (1964), 41, 451 (1964), 57, 181 (1968); Mh. Chem. 96, 369 (1965); Hungarian patent specification No. 158,091; J. Chem. Soc. 1933, 555; J. Org. Chem. 14, 204 (1949); Zh. Org. Khim 2, 1492 (1966); Chem. Abstr. 66, 46286p (1967); Dokl. Akad. Nauk. 166, 359 (1966); Khim. Geterotsikl. Soedin. 1970, 1003, 1308, 1971, 730; Chem. Abstr. 74, 12946d, 76293w (1971), 76, 25035x (1972); Chem. Ber. 104, 2984 (1971); Synthesis 1971, 423.

The 6H-2-benzopyran-6-one compounds of the general formula (IV) may also exist in the tautomeric 2-benzopyrilium-6-oxide form corresponding to the general formula (IVa),

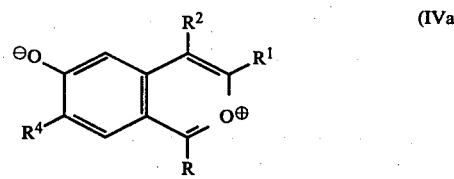

(IVa)

wherein R, R$^1$, R$^2$ and R$^4$ are as defined above. The term "a compound of the general formula (IV)" embraces each of these tautomers as well as any mixtures thereof.

Based on the results of the pharmacological studies the new 5H-2,3-benzodiazepine derivatives of the invention possess significant central nervous effects. These compounds decrease the spontaneous motor activity and potentiate the effect of narcotics.

The tests were performed on mice. In the examination of the general behaviour the animals were treated intraperitoneally with 100 mg/kg or orally with 200 mg/kg of the compound in question. The fighting behaviour test was performed according to the method of Tedeschi et al. (J. Pharm. Exp. Ther. 25, 28 /1959/). The observations concerning the general behaviour of the animals and the ED$_{50}$ values obtained in the fighting behaviour test are summarized in Table 1. In these tests 1-(3,4-dimethoxyphenyl)-4-methyl-5-ethyl-7,8-dimethoxy-5H-2,3-benzodiazepine (Grandaxin) was applied as reference substance.

TABLE 1

| Compound (No. of Example) | General behaviour (100 mg/kg i.p. and, resp., 200 mg/kg p.o., mice) | "Fighting behaviour" test on mice ED$_{50}$ mg/kg p.o. | relative activity |
|---|---|---|---|
| Grandaxin | Decrease of SMA | 64 | 1.0 |
| 4 | Decrease of SMA | 40 | 1.6 |
| 18 | Strong decrease of SMA | 40 | 1.6 |
| 22 | Decrease of SMA, catalepsy | 35 | 1.8 |
| 35 | Decrease of SMA | 60 | 1.1 |
| 37 | Strong decrease of SMA | 40 | 1.6 |
| 39 | Strong decrease of SMA | 16 | 4.0 |
| 40 | Decrease of SMA | 50 | 1.3 |
| 41 | Decrease of SMA | 37 | 1.7 |
| 42 | Decrease of SMA | 40 | 1.6 |
| 43 | Decrease of SMA | 36 | 1.8 |
| 44 | Strong decrease of SMA | 22 | 2.9 |
| 45 | Decrease of SMA | 50 | 1.3 |
| 46 | Strong decrease of SMA | 50 | 1.3 |

SMA = spontaneous motor activity

When studying the narcosis potentiating effect, the benzodiazepine compounds were administered to mice in oral dosages of 12.5, 25, 50 or 100 mg/kg, and 30 minutes later 50 mg/kg of sodium hexobarbital were injected intravenously into the animals. The percentage prolongation of the narcosis period, compared to the value observed in the control group treated with sodium hexobarbital alone, was calculated. In these tests Grandaxin was applied again as reference substance. The results are summarized in Table 2.

TABLE 2

| Compound (No. of Example) | mg/kg p.o. | Narcosis potentiating activity on mice Increase, % | Relative activity |
|---|---|---|---|
| Grandaxin | 12.5 | 17 | 1.0 |
|  | 25 | 81 | 1.0 |
|  | 50 | 114 | 1.0 |
|  | 100 | 239 | 1.0 |
| 4 | 50 | 248 | 2.17 |
| 7 | 25 | 301 | 3.71 |
| 10 | 25 | 100 | 1.23 |
|  | 50 | 185 | 1.62 |
|  | 25 | 134 | 1.65 |
| 11 | 50 | 163 | 1.43 |
|  | 12.5 | 147 | 8.65 |
| 14 | 25 | 256 | 3.16 |
|  | 50 | 750 | 6.57 |
| 18 | 12.5 | 160 | 9.41 |
|  | 25 | 377 | 4.65 |

TABLE 2-continued

| Compound (No. of Example) | mg/kg p.o. | Narcosis potentiating activity on mice | |
|---|---|---|---|
| | | Increase, % | Relative activity |
| | 50 | 1520 | 13.33 |
| 22 | 25 | 181 | 2.23 |
| | 50 | 364 | 3.20 |
| 24 | 50 | 132 | 1.16 |
| 33 | 25 | 244 | 3.01 |
| | 50 | 445 | 3.90 |
| | 25 | 90 | 1.11 |
| 35 | 50 | 173 | 1.52 |
| | 100 | 780 | 3.26 |
| | 25 | 132 | 1.62 |
| 36 | 50 | 278 | 2.44 |
| 39 | 12.5 | 135 | 7.94 |
| | 25 | 344 | 4.25 |
| | 50 | 90 | 0.79 |
| 40 | 100 | 218 | 0.91 |
| | 50 | 205 | 1.80 |
| 41 | 100 | 383 | 1.60 |
| | 25 | 204 | 2.52 |
| 42 | 50 | 347 | 3.04 |
| 43 | 25 | 234 | 2.89 |
| 44 | 12.5 | 150 | 8.82 |
| | 25 | 294 | 3.63 |
| 45 | 25 | 250 | 3.09 |
| | 12.5 | 140 | 8.24 |
| 46 | 25 | 300 | 3.70 |

The data of Tables 1 and 2 clearly demonstrate the advantageous properties of the new compounds according to the invention.

The new compounds according to the invention can be converted into pharmaceutical compositions (such as tablets, coated tablets, capsules, solutions, suspensions, injectable preparations, etc.) according to methods well known in the art, by admixing them with conventional pharmaceutical carriers, diluents and/or other additives.

The invention is elucidated in detail by the aid of the following non-limiting Examples.

EXAMPLE 1

Preparation of 1-(4-chlorophenyl)-4-methyl-7,8-dimethoxy-5H-2,3-benzodiazepine 1.13 g (2.73 mmoles) of 1-(4-chlorophenyl)-3-methyl-6,7-dimethoxy-2-benzopyrilium perchlorate are suspended in 10 ml of methanol. The suspension is heated to boiling, and 1.0 ml of 98% hydrazine hydrate is added. The mixture is evaporated, the residue is admixed with water, then filtered off and dried. 0.87 g (2.65 mmoles) of the title compound are obtained; m.p.: 188°–198° C. The crude product is recrystallized from 30 ml of ethanol to obtain 0.6312 g (1.92 mmoles, 72.5%) of a white, crystalline substance melting at 209°–211° C. $C_{18}H_{17}ClN_2O_2 = 328.8$.

EXAMPLES 2 TO 15

The process described in Example 1 is repeated with the difference that other 2-benzopyrilium salts are applied as starting substances, and the reaction is performed in methanol, ethanol or isopropanol. The following compounds are obtained (the empirical formula, molecular weight, melting point and recrystallization medium are indicated for each of the products):

Example 2: 1-phenyl-4-methyl-5-ethyl-7-methoxy-5H-2,3-benzodiazepine; $C_{19}H_{20}N_2O = 292.4$, m.p.: 162°–163° C. (isopropanol).

Example 3: 1-phenyl-4-methyl-5-ethyl-8-methoxy-5H-2,3-benzodizepine; $C_{19}H_{20}N_2O = 292.4$, m.p.: 134°–135° C. (isopropanol).

Example 4: 1-(4-methoxyphenyl)-4-methyl-5-ethyl-7,8-dimethoxy-5H-2,3-benzodiazepine; $C_{21}H_{24}N_2O_3 = 352.4$, m.p.: 157°–159° C. (isopropanol).

Example 5: 1-(3,4-dimethoxyphenyl)-4,5-dimethyl-7,8-dimethoxy-5H-2,3-benzodiazepine; $C_{21}H_{24}N_2O_4 = 368.4$, m.p.: 201°–203° C. (1:3 mixture of chloroform and isopropanol).

Example 6: 1-(3,4-dimethoxyphenyl)-4,8-dimethyl-5-ethyl-5H-2,3-benzodiazepine; $C_{21}H_{24}N_2O_2 = 336.4$, m.p.: 156°–158° C. (isopropanol).

Example 7: 1-(2-tolyl)-4-methyl-5-ethyl-7,8-dimethoxy-5H-2,3-benzodiazepine; $C_{21}H_{24}N_2O_2 = 336.4$, m.p.: 170°–171° C. (isopropanol).

Example 8: 1-(3,4-dimethoxyphenyl)-4-methyl-5-n-butyl-7,8-dimethoxy-5H-2,3-benzodiazepine hydrate; $C_{24}H_{30}N_2O_4 \cdot H_2O = 428.5$, m.p.: 93°–96° C. (ethanol).

Example 9: 1-(3,4-dimethoxyphenyl)-4-methyl-5-ethyl-8-chloro-5H-2,3-benzodiazepine; $C_{20}H_{21}ClN_2O_2 = 356.9$, m.p.: 185°–187° C. (isopropanol).

Example 10: 1-(3,4-dimethoxyphenyl)-4-methyl-5-n-propyl-7,8-dimethoxy-5H-2,3-benzodiazepine hydrate; $C_{23}H_{28}N_2O_4 \cdot H_2O = 414.5$, m.p.: 92°–96° C. (ethanol). The compound containing no crystal water melts at 143°–145° C.

Example 11: 1-(3,4-dimethoxyphenyl)-4,5-diethyl-7,8-dimethoxy-5H-2,3-benzodiazepine; $C_{23}H_{28}N_2O_4 = 396.5$, m.p.: 142°–144° C. (isopropanol).

Example 12: 1-(3,4-dimethoxyphenyl)-4-n-propyl-5-ethyl-7,8-dimethoxy-5H-2,3-benzodiazepine; $C_{24}H_{30}N_2O_4 = 410.5$, m.p.: 132°–134° C. (40% isopropanol).

Example 13: 1-(3,4-dimethoxyphenyl)-5-ethyl-7,8-dimethoxy-5H-2,3-benzodiazepine-4-carboxylic acid ethyl ester; $C_{24}H_{28}N_2O_6 = 440.5$, m.p.: 178°–180° C. (abs. ethanol).

Example 14: 1-(2-fluorophenyl)-4-methyl-5-ethyl-7,8 dimethoxy-5H-2,3-benzodiazepine; $C_{20}H_{21}FN_2O_2 = 340.4$, m.p.: 86°–88° C. (ethanol and water).

Example 15: 1-(3,4-dimethoxyphenyl)-4-ethyl-5-methyl-7,8-dimethoxy-5H-2,3-benzodiazepine; $C_{22}H_{26}N_2O_4 = 382.5$, m.p.: 157°–158° C. (isopropanol).

EXAMPLE 16

Preparation of 1-(3,4,5-trimethoxyphenyl)-4-methyl-5-ethyl-7,8-dimethoxy-5H-2,3-benzodiazepine 1.40 g (3.36 mmoles) of 2-(1-ethylacetonyl)-3',4,4',5,5'-pentamethoxybenzophenone are dissolved in 5.4 ml of isopropanol, and 0.175 ml of concentrated sulfuric acid are added dropwise to the solution. The reaction mixture is heated to boiling, stirred at this temperature for one hour, thereafter the mixture is cooled to 60° C. and 0.41 ml (8 mmoles) of 98% hydrazine hydrate are added. The resulting mixture is stirred for a further hour. 0.154 g of sodium hydrocarbonate are added in portions to the mixture, the mixture is heated to boiling, decolorized with charcoal, filtered, the filtrate is evaporated, and the residue is passed onto a filter with a total amount of 25 ml of water. 0.835 g (60.5%) of the title compound are obtained; m.p.: 152°–155° C. When recrystallized from a small amount of isopropanol the product melts at 160°–162° C. $C_{23}H_{28}N_2O_5 = 412.5$.

EXAMPLE 17

Preparation of 1-(3,4-dimethoxyphenyl)-4-methyl-7,8-dimethoxy-5H-2,3-benzodiazepine One proceeds as described in Example 16 with the difference that 2-acetonyl-3′,4,4′,5-tetramethoxybenzophenone is applied as starting substance. The title compound melts at 158°–159° C. after recrystallization from abs. ethanol. $C_{20}H_{22}N_2O_4 = 354.4$.

EXAMPLE 18

Preparation of 1-(2-chlorophenyl)-4-methyl-5-ethyl-7,8-dimethoxy-5H-2,3-benzodiazepine A mixture of 10.37 g (28.9 mmoles) of 2-(1-ethylacetonyl)-4,5-dimethoxy-2′-chlorobenzophenone, 10.5 ml of glacial acetic acid and 2.65 ml of concentrated hydrochloric acid is heated to 95° C. under stirring. The mixture is cooled to 60° C., and 2.14 ml of 98% hydrazine hydrate are added to the mixture in portions, whereupon the temperature of the mixture raises to 85° C. After 30 minutes a solution of 1.44 g of sodium hydroxide in 4.5 ml of water is added to the mixture, followed by 10 ml of methanol. The resulting solution is poured into 130 ml of water, and the separated 5H-2,3-benzodiazepine derivative is isolated. 9.04 g (88%) of the title compound are obtained; m.p.: 129°–131° C. $C_{20}H_{21}ClN_2O_2 = 356.9$. The crude product can be recrystallized e.g. from ethanol. The product with the highest purity grade melts at 147°–149° C. The rhodanide salt of the title compound ($[C_{20}H_{22}ClN_2O_2]SCN = 425.95$) melts at 169°–171° C. after recrystallization from isopropanol.

EXAMPLE 19

Preparation of 1-phenyl-4-methyl-7,8-dimethoxy-5H-2,3-benzodiazepine

One proceeds as described in Example 18 with the difference that 2-acetonyl-4,5-dimethoxybenzophenone is applied as starting substance. The title compound melts at 169°–170° C. after recrystallization from methanol, dimethyl formamide and water. $C_{18}H_{18}N_2O_2 = 294.4$.

EXAMPLE 20

Preparation of 1-(2-chlorophenyl)-4-methyl-7,8-dimethoxy-5H-2,3-benzodiazepine hydrochloride One proceeds as described in Example 18 with the difference that 2-acetonyl-4,5-dimethoxy-2′-chlorobenzopnenone is applied as starting substance. The resulting crude 1-(2-chlorophenyl)-4-methyl-7,8-dimethoxy-5H-2,3-benzodiazepine is treated with absolute ethanol containing hydrochloric acid to obtain the pure hydrochloride. $[C_{18}H_{18}ClN_2O_2]Cl = 365.5$. The title compound decomposes at 186°–188° C. after recrystallization from absolute ethanol and ether.

EXAMPLE 21

Preparation of 1-(3,4-dimethoxyphenyl)-4,7,8-trimethyl-5-ethyl-5H-2,3-benzodiazepine 5 ml of absolute ethanol containing hydrochloric acid are added to 1.33 g of crude 1-(3,4-dimethoxyphenyl)-4,7,8-trimethyl-5-ethyl-5H-2,3-benzodiazepine, a compound prepared according to the process described in Example 1, and the resulting orange red solution is evaporated. The residue is dissolved in 5 ml of water, and 0.5 g of ammonium rhodanide are added to the solution. The separated substance is filtered off, washed six times with 2 ml of water each and dried. 1.48 g of crude 1-(3,4-dimethoxyphenyl)-4,7,8-trimethyl-5-ethyl-5H-2,3-benzodiazepine rhodanide are obtained; m.p.: 132°–134° C. When recrystallized from isopropanol the slt melts at 142°–144° C. Pure title compound can be liberated from the recrystallized rhodanide by treating it with an alkali or ammonium hydroxide. $C_{22}H_{62}N_2O_2\cdot H_2O = 368.5$. The product recrystallized from isopropanol and water shrinks from 79° C.

EXAMPLE 22

Purification of 1-phenyl-4-methyl-5-ethyl-7,8-dimethoxy-5H-2,3-benzodiazepine through the rhodanide One proceeds as described in Example 21 with the difference that crude 1-phenyl-4-methyl-5-ethyl-7,8-dimethoxy-5H-2,3-benzodiazepine is applied as starting substance. The pure rhodanide of this compound melts at 175°–177° C. after recrystallization from absolute ethanol. The base liberated from the rhodanide contains crystal water ($C_{20}H_{22}N_2O_2\cdot H_2O = 340.4$) and shrinks from 77° C. (after recrystallization from ethanol and water).

EXAMPLE 23

Preparation of 1-(3,4-dimethoxyphenyl)-4-methyl-5-ethyl-7-hydroxy-8-methoxy-5H-2,3-benzodiazepine (a) 34.5 ml of 98% hydrazine hydrate are added dropwise, within 5 minutes, to a stirred solution of 115 g (0.325 mole) of 1-(3,4-dimethoxyphenyl)-3-methyl-4-ethyl-7-methoxy-6H-2-benzopyran-6-one in 115 ml of glacial acetic acid. During this operation the solution is maintained at 80° to 100° C. The solution is immersed into a water bath (95° to 100° C.) for one hour, then it is diluted with 140 ml of 2% aqueous sodium hydroxide solution and cooled. The 5H-2,3-benzodiazepine derivative separates as a beige crystalline substance. The solids are filtered off, washed four times with 50 ml of water each and dried. 111.7 g of the crude product are obtained; m.p.: 210°–212° C. To purify the crude product it is dissolved in 223 ml of dimethyl formamide at 100° to 130° C., and the solution is decolorized with 2 g of activated carbon. The carbon is filtered off and washed thrice with 50 ml of dimethyl formamide each. The solution is filtered with 1300 ml of distilled water, whereupon the pure product separates in crystalline form. 110.35 g (94%) of the title compound are obtained; m.p.: 210°–212° C. According to gas chromatographical examination the purity grade of the product is above 99%. $C_{21}H_{24}N_2O_4 = 368.4$.

The hydrochloride of the product ($C_{21}H_{25}N_2O_4Cl$) decomposes at 218°–220° C. after recrystallization from isopropanol.

(b) 1.2 ml of 98% hydrazine hydrate are added dropwise to a stirred suspension of 4.35 g (0.01 mole) of 1-(3,4-dimethoxyphenyl)-3-methyl-4-ethyl-6-hydroxy-7-methoxy-2-benzopyrilium bromide in 15 ml of 50% aqueous acetic acid at 80° to 100° C. The mixture is warmed to 90° to 100° C. and diluted with 200 ml of 10% aqueous sodium chloride solution, whereupon the crude product separates. The crude product can be purified by precipitating it with water from a dimethyl formamide or ethanol solution. The yield varies between 92% and 95%. The product melts at 210°–212° C., and no depression of melting point can be observed when admixing it with the substance prepared according to method (a).

(c) One proceeds as described in point (a) with the difference that glacial acetic acid is replaced by a tenfold volume of methanol. After one hour of boiling the solution is evaporated and the residue, treated optionally with water, is recrystallized from dimethyl formamide and water as described in point (a). The title compound, melting at 210°–212° C., is obtained with a yield of 95%.

EXAMPLES 24 TO 29

The following hydroxyphenyl-5H-2,3-benzodiazepine derivatives are prepared as described in methods (a) to (c) of Example 23:

Example 24: 1-(3-methoxy-4-hydroxyphenyl)-4-methyl-5-ethyl-7,8-dimethoxy-5H-2,3-benzodiazepine; $C_{21}H_{24}N_2O_4=368.4$, m.p.: 130°–132° C. (ethanol and water).

Example 25: 1-(4-methoxy-3-hydroxyphenyl)-4-methyl-5-ethyl-7-methoxy-8-hydroxy-5H-2,3-benzodiazepine; $C_{20}H_{22}N_2O_4=354.4$, m.p.: 143°–145° C. (ethanol and water). The perchlorate of the compound $(C_{20}H_{23}N_2O_4ClO_4)$ decomposes at 196°–198° C. after recrystallization from isopropanol.

Example 26: 1-(3-methoxy-4-hydroxyphenyl)-4-methyl-5-ethyl-7-hydroxy-8-methoxy-5H-2,3-benzodiazepine; $C_{20}H_{22}N_2O_4=354.4$, m.p.: 210°–212° C. under decomposition (dimethyl formamide and water).

Example 27: 1-(3,4-dihydroxyphenyl)-4-methyl-5-ethyl-7-hydroxy-8-methoxy-5H-2,3-benzodiazepine; $C_{19}H_{20}N_2O_4=340.4$, m.p.: 254°–255° C. under decomposition (dimethyl formamide and water). The hydrobromide of the compound $([C_{19}H_{21}N_2O_4]Br)$ decomposes at 206°–208° C. after recrystallization from ethyl acetate.

Example 28: 1-(3-methoxy-4-hydroxyphenyl)-4-methyl-5-ethyl-7,8-dihydroxy-5H-2,3-benzodiazepine; $C_{19}H_{20}N_2O_4=340.4$, m.p.: 252°–253° C. under decomposition (dimethyl formamide and water). The hydrosulfate of the compound $([C_{19}H_{21}N_2O_4]HSO_4)$ decomposes at 195°–198° C. after recrystallization from ethyl acetate.

Example 29: 1-(3,4-dihydroxyphenyl)-4-methyl-5-ethyl-7,8-dihydroxy-5H-2,3-benzodiazepine; $C_{18}H_{18}N_2O_4=326.3$, m.p.: 250°–251° C. under decomposition (dimethyl formamide and water). The hydrochloride of the compound $([C_{18}H_{19}N_2O_4]Cl)$ decomposes at 268°–270° C. after recrystallization from isopropanol.

EXAMPLE 30

Preparation of 1-(4-methoxy-3-hydroxyphenyl)-4-methyl-5-ethyl-7-hydroxy-8-methoxy-5H-2,3-benzodiazepine A mixture of 0.44 g of 1-(4-methoxy-3-acetoxyphenyl)-4-methyl-5-ethyl-7-acetoxy-8-methoxy-5H-2,3-benzodiazepine, 8 ml of ethanol, 8 ml of water and 0.4 g of potassium hydroxide is stirred in nitrogen atmosphere for 15 minutes. 50 ml of 20% aqueous sodium chloride solution and 0.6 g of ammonium chloride are added to the solution. The precipitate is separated and recrystallized from 7.5 ml of 20% aqueous dimethyl formamide. 0.23 g of pure 1-(4-methoxy-3-hydroxyphenyl)-4-methyl-5-ethyl-7-hydroxy-8-methoxy-5H-2,3-benzodiazepine are obtained; the product decomposes at 210°–212° C. This compound is identical with the product obtained according to Example 26, and no depression of melting point can be observed when admixing the two products with each other.

EXAMPLE 31

Preparation of 1-(3,4-dimethoxyphenyl)-4-formyl-5-ethyl-7,8-dimethoxy-5H-2,3-benzodiazepine 6.05 g of selenium dioxide are added within 1.5 hours to a stirred suspension of 19.1 g (0.05 mole) of 1-(3,4-dimethoxyphenyl)-4-methyl-5-ethyl-7,8-dimethoxy-5H-2,3-benzodiazepine in 150 ml of 80% aqueous dioxane at an inner temperature of 84° to 87° C. The metallic selenium is removed from the mixture by clarification, and the yellow solution is evaporated in vacuo. The thick, honey-like residue is stirred with 100 ml of water, whereupon the title compound separates as a yellow powder. The product is filtered off, washed five times with 10 ml of water each and dried in vacuo. 19.3 g (96%) of crude 1-(3,4-dimethoxyphenyl)-4-formyl-5-ethyl-7,8-dimethoxy-5H-2,3-benzodiazepine are obtained; m.p.: 103°–105° C. When recrystallized from acetone and cyclohexane the product melts at 108°–110° C. $C_{22}H_{24}N_2O_5=396.45$.

EXAMPLES 32 TO 38

The phenolic hydroxy group of 1-(3,4-dimethoxyphenyl)-4-methyl-5-ethyl-7-hydroxy-8-methoxy-5H-2,3-benzodiazepine, the compound obtained according to Claim 23, is alkylated or aralkylated in a manner known per se to obtain the following products:

Example 32: 1-(3,4-dimethoxyphenyl)-4-methyl-5-ethyl-7-n-butoxy-8-methoxy-5H-2,3-benzodiazepine; $C_{25}H_{32}N_2O_4=424.5$, m.p.: 147°–150° C. (isopropanol).

Example 33: 1-(3,4-dimethoxyphenyl)-4-methyl-5-ethyl-7-isopropoxy-8-methoxy-5H-2,3-benzodiazepine; $C_{24}H_{30}N_2O_4=410.5$, m.p.: 109°–111° C. (isopropanol).

Example 34: 1-(3,4-dimethoxyphenyl)-4-methyl-5-ethyl-7-(3-dimethylaminopropoxy)-8-methoxy-5H-2,3-benzodiazepine; $C_{26}H_{35}N_3O_4=453.6$, m.p.: 126°–128° C. (isopropanol).

Example 35: 1-(3,4-dimethoxyphenyl)-4-methyl-5-ethyl-7-sec.butoxy-8-methoxy-5H-2,3-benzodiazepine; $C_{25}H_{32}N_2O_4=425.5$, m.p.: 130°–132° C. (50% aqueous ethanol).

Example 36: 1-(3,4-dimethoxyphenyl)-4-methyl-5-ethyl-7-ethoxy-8-methoxy-5H-2,3-benzodiazepine; $C_{23}H_{28}N_2O_4=396.4$, m.p.: 125°–127° C. (50% aqueous ethanol).

Example 37: 1-(3,4-dimethoxyphenyl)-4-methyl-5-ethyl-7-n-propoxy-8-methoxy-5H-2,3-benzodiazepine; $C_{24}H_{30}N_2O_4=410.5$, m.p.: 110°–112° C. (50% aqueous ethanol).

Example 38: 1-(3,4-dimethoxyphenyl)-4-methyl-5-ethyl-7-(2-diethylaminoethoxy)-8-methoxy-5H-2,3-benzodiazepine dihydrochloride; $[C_{27}H_{39}N_3O_4]Cl_2=540.5$, m.p.: 159°–126° C. under decomposition (isopropanol).

The compounds of Examples 39 to 49 were prepared correspondingly as in Examples 1 to 38.

EXAMPLE 39

1-(3-Chlorophenyl)-4-methyl-7,8-dimethoxy-5H-2,3-benzodiazepine

M.p.: 166°–168° C. (from isopropanol).

Hydrochloride: melts at 185°–187° C. under decomposition after recrystallising from a mixture of isopropanol and ethylacetate.

EXAMPLE 40

1-(3-Chlorophenyl)-4,5-dimethyl-7,8-dimethoxy-5H-2,3-benzodiazepine

M.p.: 156°–158° C. (from isopropanol).

EXAMPLE 41

1-(3-Fluorphenyl)-4-methyl-7,8-dimethoxy-5H-2,3-benzodiazepine

M.p.: 138°–140° C. (from isopropanol).

EXAMPLE 42

1-(3-Fluorphenyl)-4-methyl-5-ethyl-7,8-dimethoxy-5H-2,3-benzodiazepine

M.p.: 122°–124° C. (from a mixture of ethanol and water).

EXAMPLE 43

1-(2-Methoxyphenyl)-4-methyl-7,8-dimethoxy-5H-2,3-benzodiazepine

M.p.: 119°–121° C. (from isopropanol).

EXAMPLE 44

1-(3-Trifluoromethyl-phenyl)-4-methyl-7,8-dimethoxy-5H-2,3-benzodiazepine

M.p.: 134°–135° C. (from a mixture of ethanol and water).

EXAMPLE 45

1-(2-Furyl)-4-methyl-7,8-dimethoxy-5H-2,3-benzodiazepine

M.p.: 155°–157° C. (from a mixture of dimethyl formamide and water).

EXAMPLE 46

1-(3-Methoxyphenyl)-4-methyl-7,8-dimethoxy-5H-2,3-benzodiazepine

M.p.: 133°–135° C. (from isopropanol).

EXAMPLE 47

1-(3-Nitrophenyl)-4-methyl-7,8-dimethoxy-5H-2,3-benzodiazepine

Melts at 196°–198° C. (from a mixture of dimethyl formamide and water).

EXAMPLE 48

1-(2-Thienyl)-4-methyl-7,8-dimethoxy-5H-2,3-benzodiazepine, HCl

Melts at 188°–190° C. (from ethanol-acetone).

EXAMPLE 49

1-(2-Thienyl)-4-methyl-5-ethyl-7,8-dimethoxi-5H-2,3-benzodiazepine-HCl

Melts at 147°–149° C. (from ethanol-acetone).

EXAMPLE 50

(A) Tablets containing 10 mg of 1-(3-chlorophenyl)-4-methyl-7,8-dimethoxy-5H-2,3-benzodiazepine

| Composition of 1 tablet: | |
| --- | --- |
| Active agent | 10.0 mg |
| Magnesium strearate | 1.2 mg |
| Talc | 3.6 mg |
| Gelatine | 3.0 mg |
| Microcystalline cellulose | 10.0 mg |
| Corn starch | 12.2 mg |
| Lactose | 80.0 mg |
| | 120.0 mg |

(B) Dragées containing 10 mg of 1-(3-chlorophenyl)-4-methyl-7,8-dimethoxy-5H-2,3-benzodiazepine

| Composition of 1 dragée core: | |
| --- | --- |
| Active agent | 10.0 mg |
| Magnesium stearate | 0.5 mg |
| Lactose | 19.0 mg |
| Corn starch | 8.0 mg |
| Polyvinylpyrrolidone | 2.5 mg |
| | 40.0 mg |

The dragee core is coated in the usual way with sugar and talc and then it is polished by using bee wax. The dragee weighs 70 mg.

What we claim is:

1. A compound of the formula

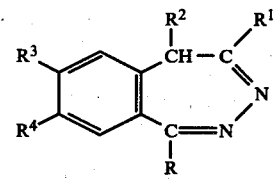

wherein
R is phenyl having a trifluoromethyl or a halogen substituent,
$R^1$ is methyl,
$R^2$ is hydrogen,
$R^3$ is methoxy and $R^4$ is methoxy, or a pharmaceutically acceptable acid addition salt thereof.

2. A compound as claimed in claim 1, which is 1-(3-chlorophenyl)-4-methyl-7,8-dimethoxy-5H-2,3-benzodiazepine or a pharmaceutically acceptable acid addition salt thereof.

3. A compound as claimed in claim 1, which is 1-(3-trifluoromethylphenyl)-4-methyl-7,8-dimethoxy-5H-2,3-benzodiazepine or a pharmaceutically acceptable acid addition salt thereof.

* * * * *